(12) United States Patent
Knepshield et al.

(10) Patent No.: US 6,821,266 B2
(45) Date of Patent: Nov. 23, 2004

(54) SYRINGE (75) Inventors: William R. Knepshield, Kennedyville, MD (US); Abrar Solatch, West Chester, PA (US)

(73) Assignee: U.S. Technology, Inc., West Chester, PA (US)

( * ) Notice: Subject to any disclaimer, the term of this patent is extended or adjusted under 35 U.S.C. 154(b) by 0 days.

(21) Appl. No.: 10/292,663

(22) Filed: Nov. 12, 2002

(65) Prior Publication Data

US 2004/0092871 A1 May 13, 2004

(51) Int. Cl.[7] .............................................. A61M 5/00
(52) U.S. Cl. ...................................... 604/110; 604/220
(58) Field of Search ............................... 604/193–199, 604/263, 208, 209, 210, 218, 222, 240, 242, 243, 256, 110, 158, 181, 187, 220

(56) References Cited

U.S. PATENT DOCUMENTS

| | | |
|---|---|---|
| 4,927,414 A | 5/1990 | Kulli |
| 4,950,241 A | 8/1990 | Ranford |
| 4,995,870 A | 2/1991 | Baskas |
| 5,125,899 A | 6/1992 | Frignoli |
| 5,290,233 A | 3/1994 | Campbell |
| 5,328,475 A | 7/1994 | Chen |
| 5,338,304 A | 8/1994 | Adams |
| 5,431,631 A | 7/1995 | Lu |
| 5,431,632 A | 7/1995 | Lu |
| 5,533,975 A | 7/1996 | Lu |
| 5,569,203 A | 10/1996 | Chen |
| 5,575,774 A | 11/1996 | Chen |
| 5,578,015 A | 11/1996 | Robb |
| 5,772,687 A | 6/1998 | Saito |
| 5,968,020 A | 10/1999 | Saito |
| 5,993,419 A | 11/1999 | Lo et al. |
| 6,033,385 A | 3/2000 | Liu |
| 6,402,721 B1 * | 6/2002 | Lo .............................. 604/110 |
| 6,530,903 B2 | 3/2003 | Wang et al. |

* cited by examiner

Primary Examiner—Brian L. Casler
Assistant Examiner—Kevin C. Sirmons
(74) Attorney, Agent, or Firm—Howson and Howson (57) ABSTRACT

In a syringe, in which a needle assembly is engaged by a plunger and withdrawn into a syringe barrel for safe disposal, the plunger slides in a resilient insert secured at the proximal end of the barrel. The insert engages an annular ridge near the distal end of the plunger when the plunger, with the needle assembly attached to it, is fully withdrawn, thereby securely locking the plunger to the barrel, and reliably preventing distal movement of the plunger after the needle assembly is withdrawn into the interior of the barrel. The part of the plunger that protrudes proximally from the barrel may then be snapped off.

2 Claims, 9 Drawing Sheets

SYRINGE

FIELD OF THE INVENTION

This invention relates to syringes, and more particularly to improvements in safety syringes of the kind in which a needle assembly can be withdrawn into a safe location within the barrel of the syringe after use.

BACKGROUND OF THE INVENTION

Safety syringes in which the needle can be withdrawn into the barrel are described in numerous U.S. patents, including the following U.S. patents:

U.S. Pat. No. 4,927,414 May 22, 1990
U.S. Pat. No. 4,950,241 Aug. 21, 1990
U.S. Pat. No. 4,995,870 Feb. 26, 1991
U.S. Pat. No. 5,125,899 Jun. 30, 1992
U.S. Pat. No. 5,290,233 Mar. 1, 1994
U.S. Pat. No. 5,328,475 Jul. 12, 1994
U.S. Pat. No. 5,338,304 Aug. 16, 1994
U.S. Pat. No. 5,431,631 Jul. 11, 1995
U.S. Pat. No. 5,431,632 Jul. 11, 1995
U.S. Pat. No. 5,533,975 Jul. 9, 1996
U.S. Pat. No. 5,569,203 Oct. 29, 1996
U.S. Pat. No. 5,575,774 Nov. 19, 1996
U.S. Pat. No. 5,578,015 Nov. 26, 1996
U.S. Pat. No. 5,772,687 Jun. 30, 1998
U.S. Pat. No. 5,968,020 Oct. 19, 1999
U.S. Pat. No. 5,993,419 Nov. 30, 1999
U.S. Pat. No. 6,033,385 Mar. 7, 2000

Known syringes having a needle withdrawal feature have a number of disadvantages that have inhibited them from wide acceptance.

In most of the known syringes of this type, accidental premature interlocking of the plunger with the needle assembly can occur when the plunger is moved forward. In others, complicated measures are necessary to avoid premature interlocking.

Another problem is that the releasable connection between the needle base and the syringe barrel can be too weak, so that the needle assembly can be pushed into the barrel in the process of inserting the needle through the stopper of a vial or through the skin of a patient. Alternatively, the connection between the needle base and the syringe barrel can be stronger than the connection made between the plunger and the needle assembly, in which case the latter connection can be broken as the plunger is withdrawn in an attempt to pull the needle assembly into the barrel. Still another problem is that, even after the needle is withdrawn into the syringe barrel, it is possible for the needle to be returned to its projecting condition, either by movement of the plunger in the distal direction, or in other ways, such as by tampering, if the plunger is broken off.

Known safety syringes are also subject to various other disadvantages, including complexity of construction, high manufacturing costs, inadequate strength, lack of versatility, and other deficiencies in safety and reliability. Moreover, most known safety syringes require the manipulations in addition to, or different from, the manipulations carried out in the use of a conventional non-safety syringe.

Among the objects of this invention, therefore, are the avoidance of some or all of the aforementioned problems, and the achievement of a safe, simple, inexpensive, reliable, versatile, and otherwise generally acceptable safety syringe.

BRIEF SUMMARY OF THE INVENTION

The safety syringe according to the invention comprises an elongated barrel having proximal and distal ends, a cylindrical interior wall, and openings at the proximal and distal ends. A standard needle assembly, comprising a hollow needle and a needle base, is provided on the barrel, the needle base being removably held in the distal end opening of the barrel with the needle projecting therefrom externally of the barrel in the direction of barrel elongation. A plunger extends through the proximal end opening of the barrel and has a resilient plunger tip sealingly engaged with the cylindrical interior wall of the barrel and slidable along said wall to draw fluid into the barrel through the needle and to expel fluid from the interior of the barrel through the needle. Interlockable elements on the needle base and plunger are provided for connecting the needle base to the plunger when the plunger tip is moved in the distal direction past a predetermined position, so that the needle base and plunger may be connected with each other, and the needle assembly can be drawn into the interior of the barrel by movement of the plunger in the proximal direction.

A latch connects the plunger with the barrel when the plunger tip is adjacent the distal end of the barrel but not past said predetermined position in the distal direction. The latch preferably comprises a tab hinged by a live hinge to a finger flange of the barrel, and engageable with a notch formed in the plunger at a position such that, when the latch is engaged with the notch, it prevents distal movement of the plunger to a position at which the interlockable elements of the needle base and the plunger become engaged. The latch, however, is readily released by proximal movement of the plunger. Thus, upon proximal movement of the plunger to draw fluid into the barrel through the needle, and distal movement of the plunger to expel fluid from the barrel through the needle, the interlockable elements of the needle base and plunger may be operated to connect the plunger to the needle base for withdrawal of the needle assembly into the barrel. The latch reliably prevents accidental premature interlocking of the plunger with the needle assembly, yet is easily disabled as the plunger is pulled back to draw fluid into the syringe barrel through the needle.

A projection is provided on the plunger adjacent the plunger tip, and a resilient insert is secured to the barrel adjacent the proximal end of the barrel. The plunger extends through the resilient insert, and the resilient insert permits movement of the plunger in the direction of elongation of the barrel. The resilient insert has a cam surface engageable by the projection on the plunger to expand the insert when the plunger is withdrawn past a predetermined position in the proximal direction. The cam surface, however, permits resilient contraction of the insert when the plunger moves farther in the proximal direction. The plunger and insert have latching surfaces which move past each other when the insert is expanded by the engagement of the cam surface by the projection. The latching surfaces are engageable with each other when the insert resiliently contracts after the plunger makes said movement farther in the proximal direction, to prevent distal movement of the plunger after the needle assembly is withdrawn into the interior of the barrel. The resilient insert reliably prevents distal movement of the plunger after the needle assembly is withdrawn into the interior of the barrel.

In a preferred embodiment of the invention, the resilient plunger tip is hollow, and the interlockable elements include a barbed, sharp-tipped, projection projecting in the proximal direction from the needle base and a pair of opposed, resilient jaws formed on the plunger and located within the hollow plunger tip. The sharp=tipped projection is capable of penetrating the membrane which forms the face of the hollow plunger tip, and the resilient jaws have hook-shaped tips, spaced from each other by a distance less than the width of the barbed, sharp-tipped projection. The jaws are movable apart from each other by the projection, and engageable with the barbs of the projection to connect the needle base to the plunger. These interlocking elements securely connect the needle base to the plunger and ensure that the needle assembly will be reliably withdrawn into the barrel.

Other objects, details and advantages of the invention will be apparent from the following detailed description when read in conjunction with the drawings.

DETAILED DESCRIPTION OF THE PREFERRED EMBODIMENT

Figure 1A:
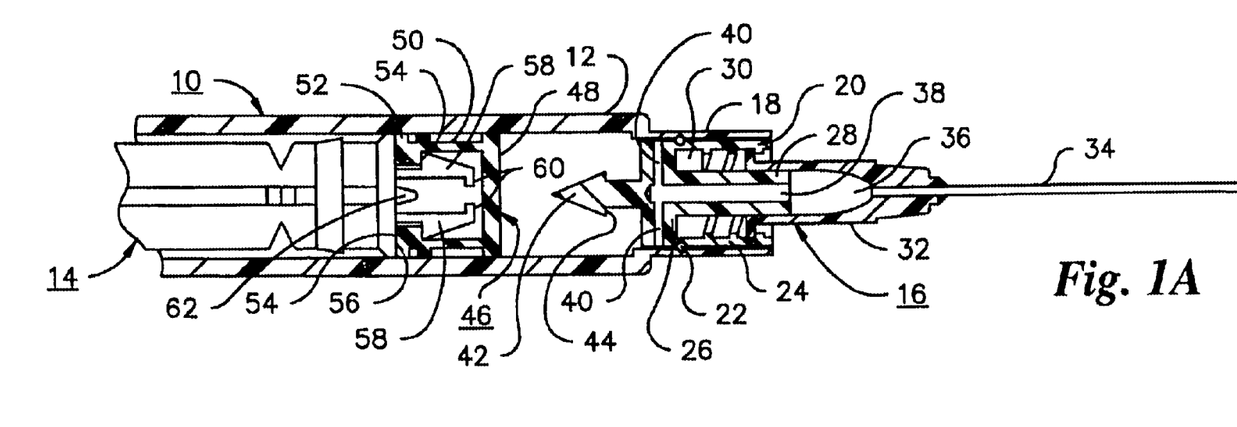
FIGS. 1A and 1B are fragmentary longitudinal sections of the proximal and distal parts of a syringe in accordance with the invention, showing the syringe in a condition as supplied to the user.
Figure 1B:
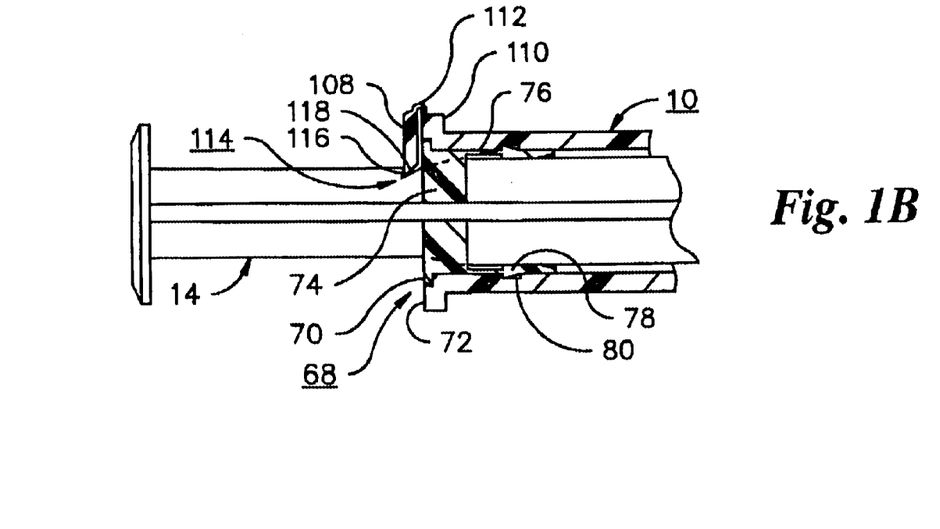

As shown in FIGS. 1A and 1B, the syringe comprises an elongated barrel 10 having a cylindrical interior wall 12, a plunger 14, which is longitudinally movable within the barrel, and a needle assembly 16 at the distal end of the barrel.

A neck 18, formed as a unitary part of the barrel at the distal end receives a fitting 20, which is preferably retained in the neck by the cooperation of a resilient O-ring 22 and opposed grooves in the fitting and neck respectively. The diameter of the interior of the neck is preferably somewhat smaller than the diameter of the interior wall 12 of the barrel in order to provide an internal shoulder. After the needle is withdrawn into the interior of the barrel, the needle will be tilted to the side in a manner to be described below. If an attempt is made to force the plunger forward the shoulder will engage the tip of the tilted needle, causing the needle to bend, thereby preventing the needle from projecting out of the barrel.

An outer wall 24 of the fitting 20 conforms to the shape of the interior of the neck 18, and the fitting 20 has a rear wall 26 and a tubular projection 28 which extends in the distal direction from the rear wall 26. A space 30 is provided between the projection 28 and the wall 24, and the interior surface of the wall 24 is provided with Luer threads for engagement with the hub 32 at the proximal end of a needle cannula 34. The unit consisting of hub 32 and needle cannula 34 is preferably of a standard design and usable in any of a variety of conventional syringes. The hub and needle unit can be supplied separately from the fitting 20, and connected to the fitting by engagement of the Luer threads in the usual manner. The projection 28 fits into a space 36 within the hub.

An axial fluid passage 38 inside the projection communicates with radial fluid passages 40 in the rear wall 26. The outer ends of these radial passages are spaced from the interior of the neck 18 so that fluid can flow in either direction along the path consisting of the interior of the barrel 10, passages 40 and 38, space 36 and the needle cannula 34.

The fitting 20 and the hub 32 together constitute a needle base. The needle base together with the needle cannula constitute the needle assembly 16. The needle assembly is retained in the neck 18 by the cooperation of the O-ring 22 and the opposed grooved neck and fitting so that an axial force having a magnitude exceeding a predetermined magnitude must be exerted on the needle assembly in order to disengage the needle base from the neck. This predetermined magnitude should substantially exceed the maximum magnitude of force exerted on the needle when inserted through the stopper of a vial, or in the administration of an injection.

As shown in FIG. 1A, the fitting 20 has an sharp-tipped projection 42 extending from it in the proximal direction into the interior of the barrel 10. The tip of the projection 42 is in the form of a cone, and the outer portion 44 of the base of the cone serves as a barb for engagement with the plunger.

The plunger 14 is preferably molded with a cross-shaped cross-section, and is fitted with a resilient tip or stopper 46. The stopper is a cup-shaped, hollow, elastomeric element having a face 48, which is in sealing engagement with the cylindrical interior wall 12 of the barrel. An intermediate portion of the stopper is a cylindrical wall 50, spaced from the interior wall of the barrel, and the rear portion of the plunger has an outwardly extending flange 52 in sealing engagement with the interior wall of the barrel. Flange 52 has an annular groove, which facilitates sealing engagement of the flange with the interior wall of the barrel. The stopper also has an inwardly extending flange 54, held in engagement with an end face 56 of the plunger by resilient fingers 58. The fingers are preferably unitary with the plunger, and extend in the distal direction from face 56. As shown in FIG. 1A, the engagement of the fingers with the inwardly extending flange 54 secures the stopper 46 to the plunger.

Figure 2:
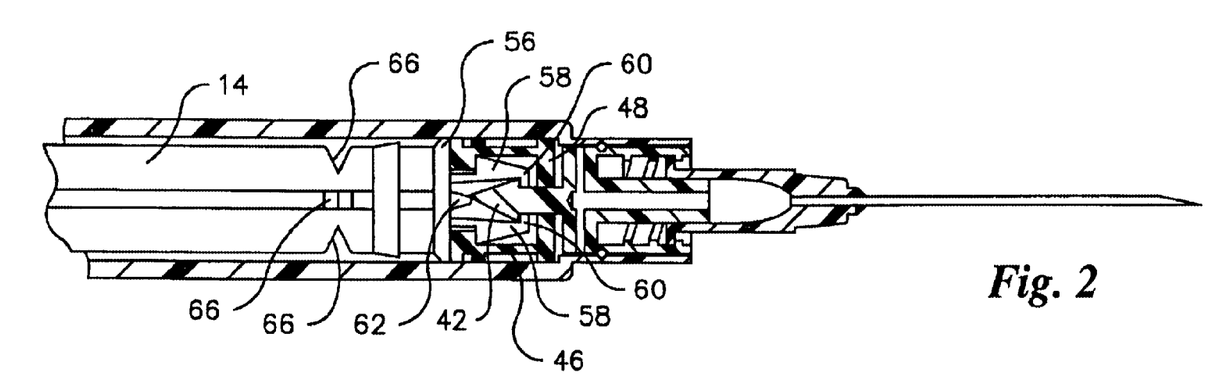
FIG. 2 is a fragmentary longitudinal section of the distal end of the syringe, showing the plunger in engagement with the needle assembly before the plunger is withdrawn to draw the needle assembly into the interior of the barrel.
Figure 3:
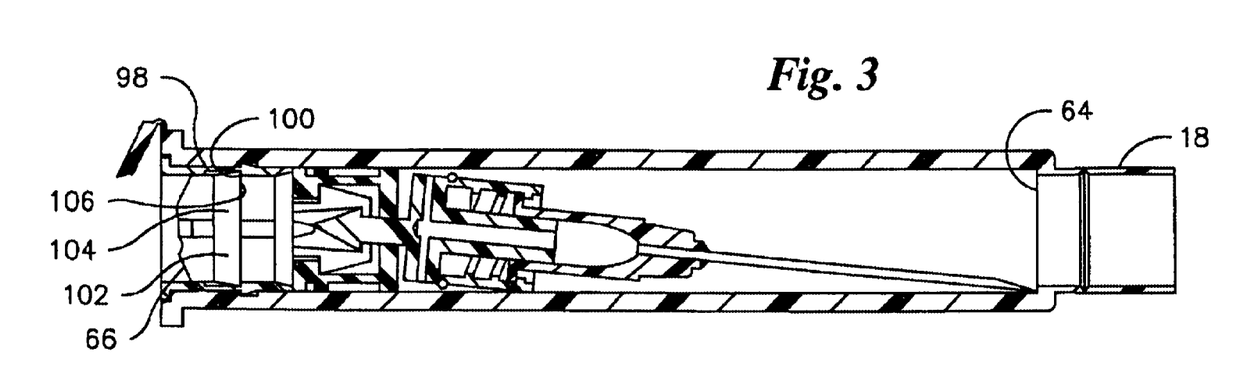
FIG. 3 is a longitudinal section showing the syringe in a condition ready for disposal.

The fingers 58 have opposed hook-shaped ends 60, which are spaced from each other by a distance less than the diameter of the base of the conical projection 42. As shown in FIG. 2, when the plunger is pushed in the distal direction as far as possible, projection 42 penetrates the face 48 of the stopper, and then acts as a cam on the hook-shaped ends 60 of fingers 58, forcing the fingers apart from each other until the hooks pass over the edge of the base of the conical tip and snap inwardly so that the plunger and the needle base are firmly connected to each other. The conical tip of projection 42, engages projection 62, which is formed on the center of face 56, between the fingers 58. When the engagement of the conical tip of projection 42 and projection 62 inside the stopper 46 first occurs, the projection 62 is deflected as shown in FIG. 2. When the plunger is withdrawn, as shown in FIG. 3, the needle assembly is disengaged from the neck 18 and withdrawn into the barrel. The engagement of the conical tip with projection 62 causes the needle assembly to tilt, as shown in FIG. 3, so that the tip of the needle is positioned opposite to a shoulder 64 where neck 18 meets the main body of the barrel 10. Therefore, even if the needle assembly is able to be pushed in the distal direction, the engagement of the needle with the shoulder will cause the needle to bend rather than project out through the neck.

Each of the arms of the cross-shaped cross-section of the plunger 14 is notched, there being four notches 66 located a short distance in the proximal direction from the stopper.

An insert 68 is located at the proximal end of the barrel, as shown in FIG. 1B. The insert has a flange 70, which engages a face 72 at the proximal end of the barrel to prevent the insert from traveling into the barrel. The insert is cup-shaped, its principal parts being an end wall 74 and a generally cylindrical side wall 76. The side wall has a radially outwardly projecting annular ridge 78, having a wedge-shaped cross-section. In the assembly of the syringe, the insert 68 is pressed into the opening at the proximal end of barrel 10. As the flange 70 comes into engagement with the end face 72 of the barrel, the ridge 78 snaps into an annular groove 80 formed on the interior wall of the barrel, so that the insert 68 is locked in place. The insert can be rotatable in the barrel.

Figure 4:
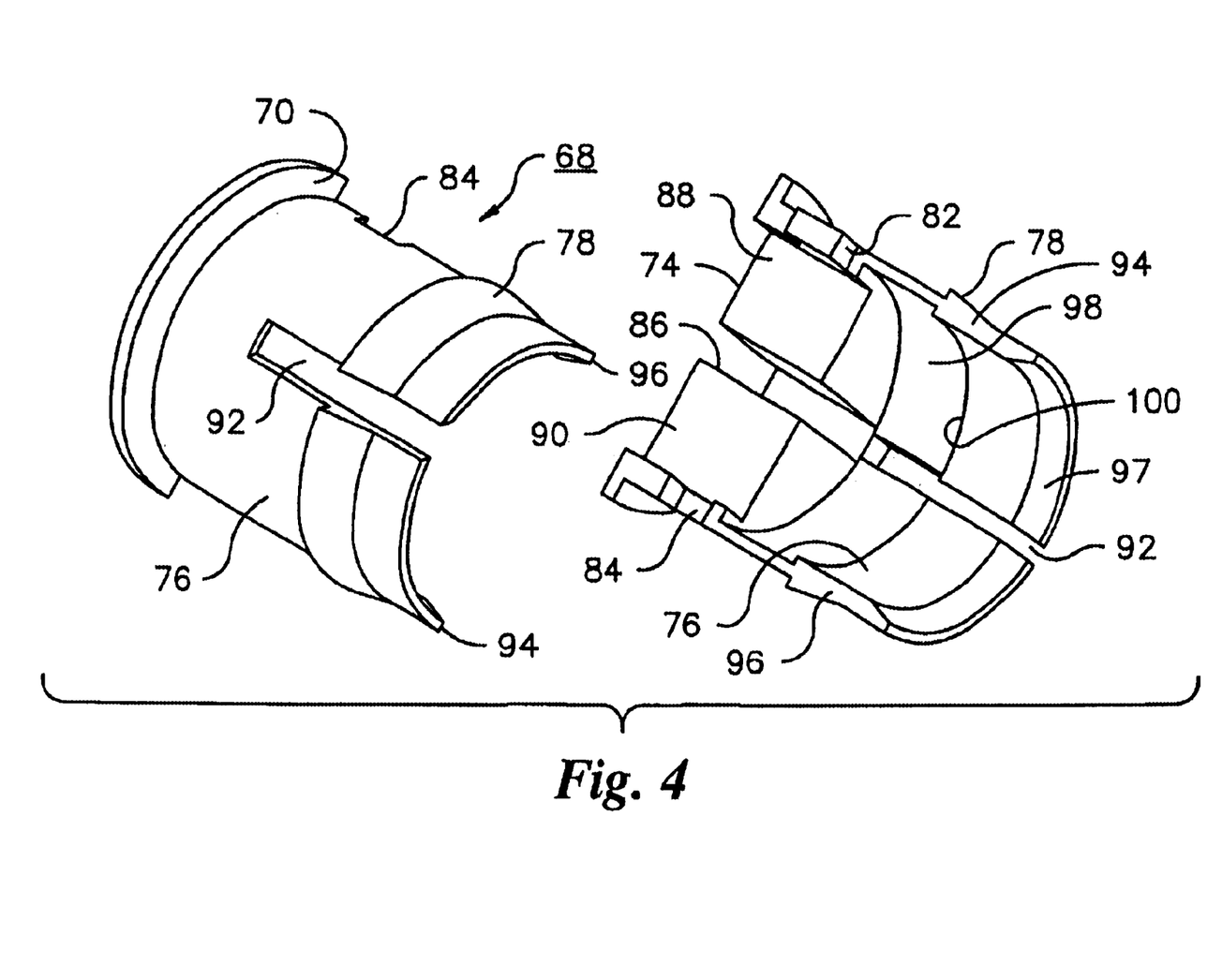
FIG. 4 is an exploded view showing the details of the resilient insert for holding the plunger in its withdrawn condition.

The details of the insert structure are shown in FIG. 4, where it is seen that the insert is composed of two identical molded parts which fit together by the engagement of a tab on each part, with a recess on the other. One of the tabs 82, and both of the recesses 84, are shown in FIG. 4.

Slots are provided in the respective parts of the end wall 74 to receive, slidably, two opposite the arms of the plunger cross-section, one such slot, 86, being shown in FIG. 4. Slots for the other two arms are provided by spaced, opposed faces of the parts of the end wall 74, two such faces, 88 and 90, being shown in FIG. 4.

Each of the two parts of the insert is split by a longitudinal slot 92, to provide flexibility, allowing the insert to fit into the proximal end of the barrel. Edges 94 and 96 of each part of the insert are also spaced from corresponding, opposed edges 96 and 94 on the other part for the same reason.

At the distal edge of the insert, the interior wall is tapered to provide a cam surface 97, which, in cooperation with an annular ridge on the plunger causes the insert to expand as the plunger is pulled in the proximal direction.

Inside the insert, an annular groove 98 is formed between end wall 74 and a shoulder 100. As shown in FIG. 3, when the plunger is fully withdrawn so that the needle is pulled into the interior of the barrel, ridge 102 on the plunger, which has a conical outer surface 104 and an annular base 106 disposed in a radial plane, snaps into the groove 98. Engagement of an outer part of base 106 with shoulder 100 securely locks the plunger to the insert, preventing the plunger from being moved in the distal direction. Therefore, the needle cannot be made to project from the barrel by pushing on the plunger.

Thus, the conical outer surface 104 and annular base 106 of ridge 102 on the plunger, together with shoulder 100, constitute means for permitting movement of the plunger in a proximal direction to a position in the barrel in which the needle assembly is withdrawn into the interior of the barrel, and for securely locking the plunger in said position in the barrel and thereby preventing the plunger from being pushed in the distal direction after the needle assembly is withdrawn into the interior of the barrel.

The insert, which is preferably molded from a suitable synthetic resin, can be color-coded in accordance with the capacity of the syringe barrel into which it fits. In this way, syringes having different capacities can be readily distinguished from one another.

In use, when the plunger is withdrawn and locked to the insert as shown in FIG. 3, the plunger may be broken off at notches 66, and the broken-off part discarded, leaving the remaining part of the plunger practically inaccessible inside the insert 68.

The syringe is preferably supplied to the user with the plunger in the position shown in FIGS. 1A and 1B, that is, with the stopper 46 near, but spaced from, projection 42. A locking tab 108, flexibly connected to a finger flange 110 by a molded live hinge 112, is engaged with a notch 114 in one of the arms of the cross-shaped cross-section of the plunger 14. In this case the notch 114 is shaped so that it is composed of a radial edge 116, engageable with the proximal face of the tab, and an inclined edge 118, which serves to cam the tab out of the way when the plunger is pulled in order to draw fluid into the barrel through the needle. With the tab thus moved out of the way, the plunger can be pushed forward for the administration of an injection. The live hinge, the tab and the finger flange should be molded with the tab positioned so that it extends generally away from the axis of the barrel in the radial direction. The material of the live hinge (which will ordinarily be integrally molded with the tab 108 and the finger flange 110 and therefore of the same composition) should have some resilience, so that it remain clear of the radial edge 116 of the notch when released from the notch by the action of the inclined edge 118.

Continued forward movement of the plunger causes the projection 42 to penetrate the stopper and become engaged with fingers 58 as described previously, so that the needle assembly can be withdrawn into the barrel, to the position shown in FIG. 3, by pulling on the plunger.

Figure 5:
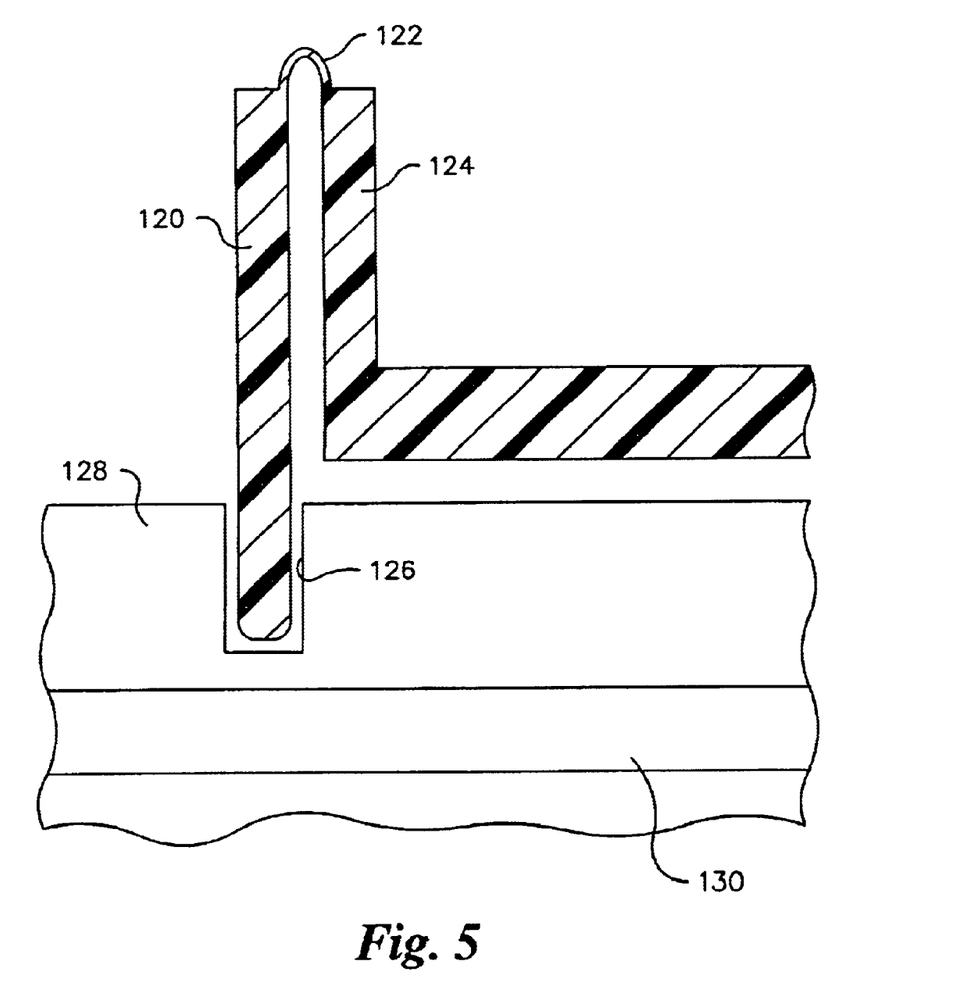
FIGS. 5–10 are fragmentary sectional views showing alternative embodiments of the latching device at the proximal end of the barrel of the syringe.

FIG. 5 shows a first modification of the tab structure, in which a tab 120, connected by an integrally molded live hinge 122 to a finger flange 124, is engaged with a rectangular notch 126 in an arm 128 of a cross-shaped plunger 130. This modification provides superior resistance to spontaneous disengagement of the tab from the plunger, but requires some flexibility in the tab or plunger, which can be achieved by an appropriate selection of materials or dimensions.

Figure 6:
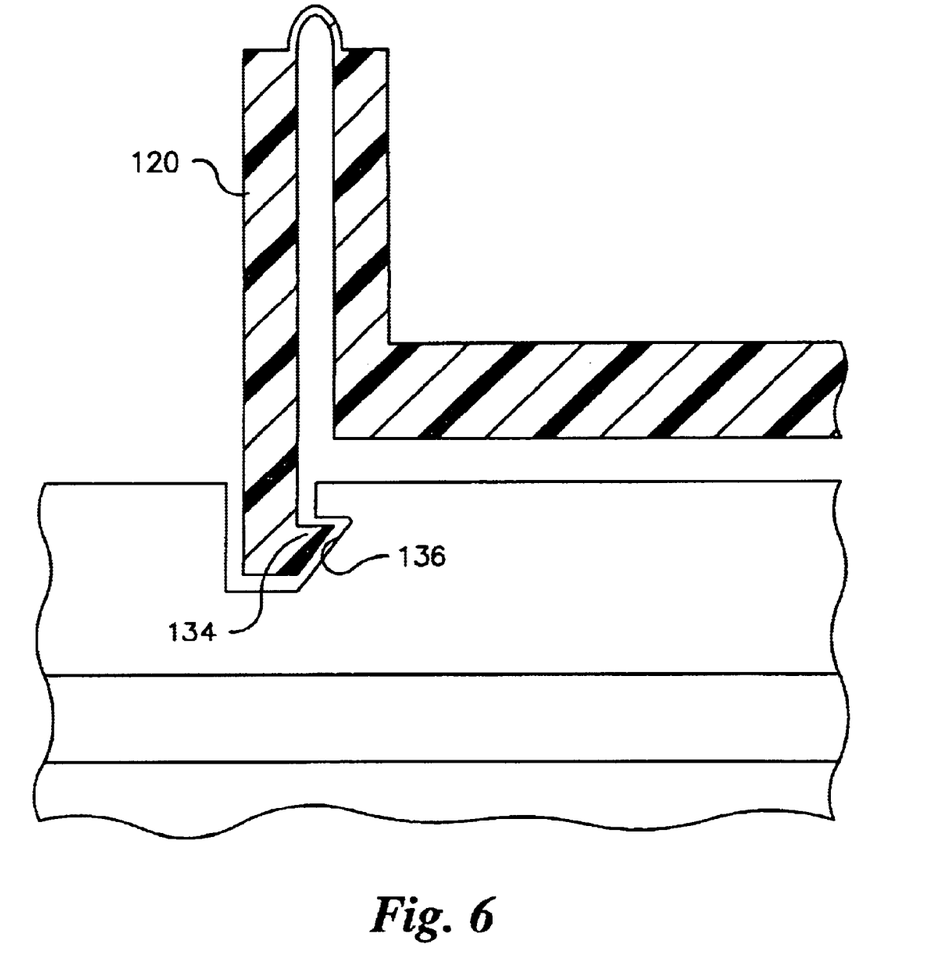

The modification shown in FIG. 6 is similar to the modification shown in FIG. 5, except that a tab 132 has a hook-like tip 134, which is engaged with an undercut notch 136 in the plunger.

Figure 7:
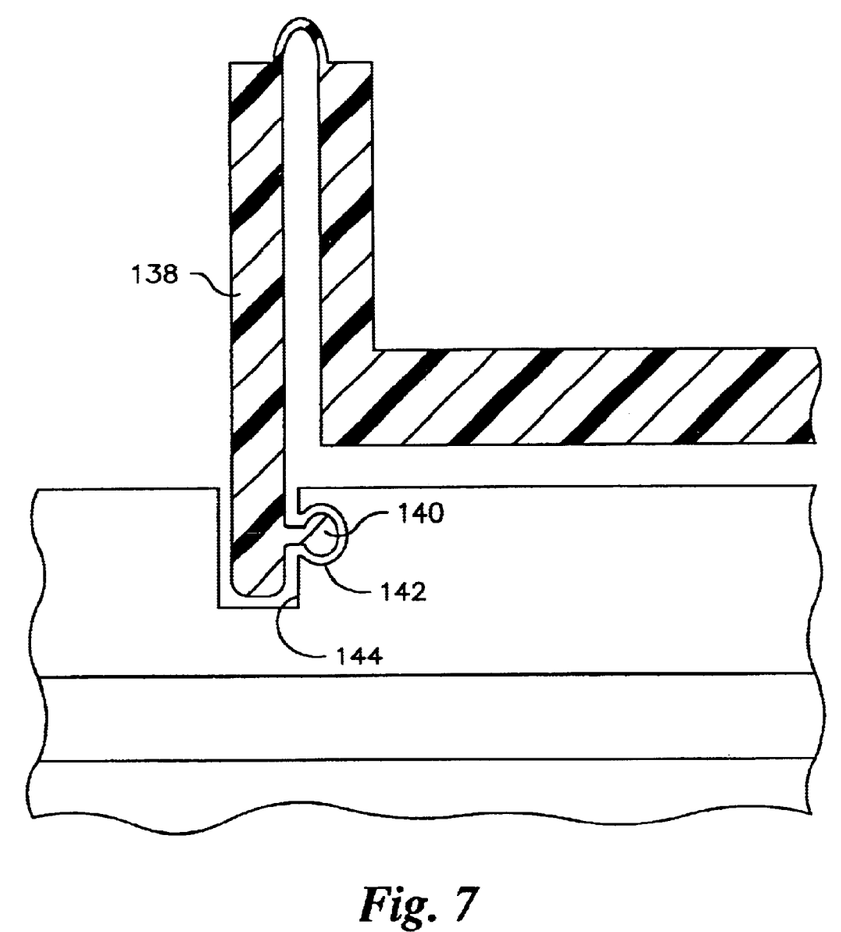

The modification shown in FIG. 7 is similar to the modification shown in FIG. 6, except that the tab 138 has a distally extending bulbous projection 140, which is engaged, by a snap fit, with an undercut recess 142 in a notch 144 formed in an arm of the plunger.

Figure 8:
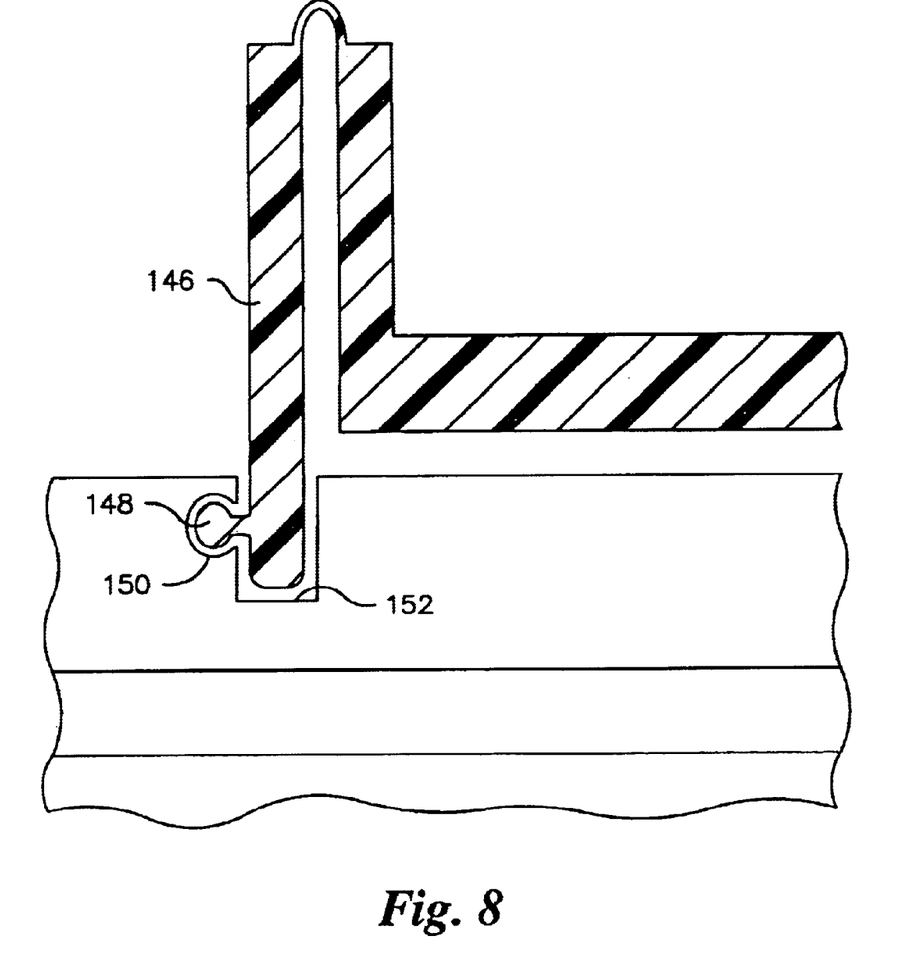

The modification shown in FIG. 8 is similar to the modification shown in FIG. 7, except that the tab 146 has a proximally extending bulbous projection 148, which is engaged with an undercut recess 150 formed on the proximal side of a notch 152.

Figure 9:
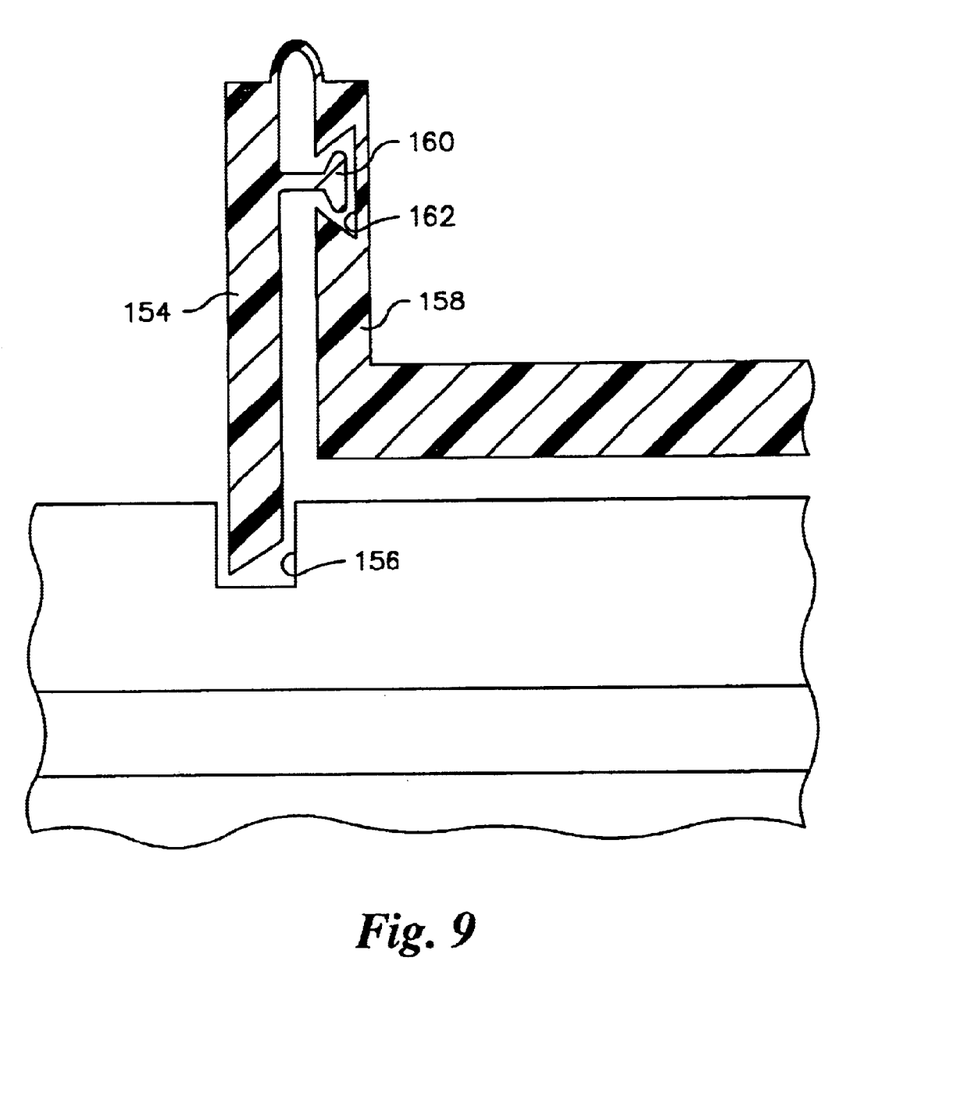
Figure 10:
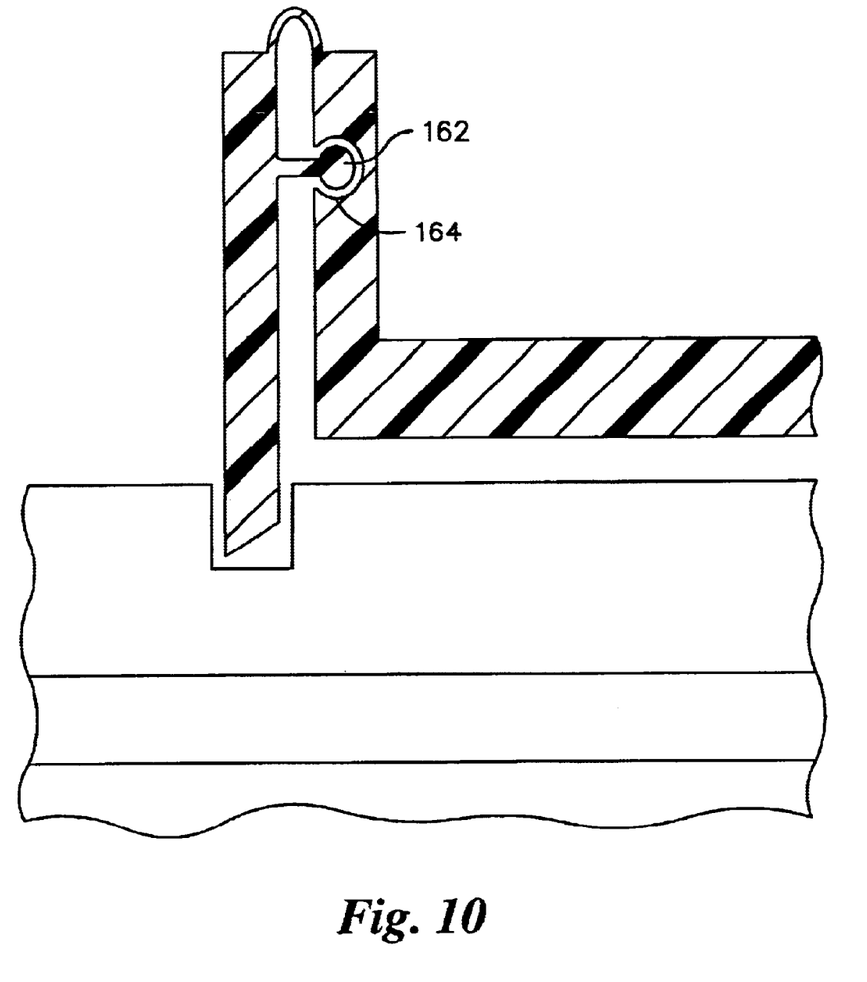

In still another modification, shown in FIG. 9, a tab 154, which engages a notch 156 in the plunger, is releasably held in parallel relation to the finger flange 158 by a flattened projection 160, which is engaged, by a snap fit, in an undercut recess 162 in the finger flange. FIG. 10 shows a similar modification, in which the projection 162 is a bulbous projection, engaged in a conforming recess 164 in the finger flange. In FIGS. 9 and 10, the recesses which receive the projections are blind holes. However, if the projections on the tabs are extended, through holes can be provided instead, for cooperation with the projections.

In each of the modifications shown in FIGS. 6–10, when the plunger is withdrawn, distortion of the projection on the tab and of its mating recess takes place to allow disengagement of the tab from the plunger.

As will be apparent from the above description, the syringe according to the invention has significant advantages over conventional syringes, and over known syringes having a needle withdrawal feature. First, the latch for preventing distal movement of the plunger, reliably prevents accidental premature interlocking of the plunger with the needle assembly, yet is easily disabled as the plunger is pulled back to draw fluid into the syringe barrel through the needle. Second, the interlocking elements on the needle base and plunger, which include a barbed, sharp-tipped, projection on the needle base for penetrating a hollow plunger tip, and a pair of opposed, resilient jaws located within the plunger tip for engaging the barbs of the projection, securely connect the needle base to the plunger. The secure connection ensures that the needle assembly will be reliably withdrawn into the barrel. Third, the resilient insert at the proximal end of the barrel securely locks the plunger to the barrel, reliably preventing distal movement of the plunger after the needle assembly is withdrawn into the interior of the barrel. This ensures that the needle assembly will remain in place inside the barrel. The part of the plunger that protrudes proximally from the barrel may then be snapped off. Fourth, the needle assembly allows for the use of standard needles. The stopper construction also avoids leakage, and minimizes dead space from which medication drawn into the syringe cannot be injected. Other advantages afforded by the invention include simplicity of construction, inexpensive manufacture, strength, safety, reliability, and versatility.

Numerous modifications can be made to the syringes as described above.

For example, the releasable connection of the base of the needle base to the neck of the barrel can be achieved by various arrangements of one or more O-rings and grooves. The grooves can be in the neck of the barrel, in the needle base, or in both the neck and the needle base. The grooves can be of various shapes, including a rectangular cross-section, a V-shaped cross-section, or a U-shaped cross-section, for example. An annular projection can be formed as a unitary part of the needle base, or as a unitary part of the neck, in which case, the O-ring can be eliminated altogether. Various other releasable connections, such as frictional connections and bonded connections, can also be utilized as alternatives to the groove and O-ring combination.

The plunger can be tapered in such a way that, when it is withdrawn, it pushes the locking tab, e.g., tab 108, outward to ensure against reengagement of the locking tab with the notch in the plunger when the plunger is pushed forward. Moreover, instead of the snap fit versions of the latch shown in FIGS. 9 and 10, an alternative can be adopted in which the projection is formed on the finger flange or otherwise on the proximal end of the barrel, and a mating recess for receiving the projection by a snap fit is formed on the hinged tab.

Although the hollow plunger tip preferably has a membrane forming its face, the membrane can be eliminated if dead space and wastage of medication can be tolerated.

The projection 42 can take various shapes other than conical, and various alternatives to the resilient fingers, such as one or more hooks, can be used to engage the projection 42 on the needle assembly 16. As a further alternative, since the insert 68 can be rotatable in the barrel, the resilient fingers and barbed projection can be replaced by an engagement mechanism, such as mutually engaging threads or a bayonet configuration, by which the plunger can be locked to the needle assembly by rotation of the plunger.

For versatility, and to allow for the use of standard needles of the kind used with conventional syringes, the needle assembly is preferably a two part assembly including a fitting removably connected to a needle base which is permanently attached to a needle. However, as an alternative, the needle hub itself can be configured so that it is directly engageable with the neck of the syringe barrel.

Still other modifications may be made to the apparatus and method described above without departing from the scope of the invention as defined in the following claims.

What is claimed is:

1. A safety syringe comprising:

an elongated barrel having proximal and distal ends, a cylindrical interior wall, and openings at said proximal and distal ends;

a needle assembly comprising a hollow needle and a needle base, the needle base being removably held in the distal end opening of the barrel with the needle projecting therefrom externally of the barrel in the direction of elongation of the barrel;

a plunger extending through the proximal end opening of the barrel and having a resilient plunger tip sealingly engaged with the cylindrical interior wall of the barrel and slidable along said wall to draw fluid into the barrel through the needle and to expel fluid from the interior of the barrel through the needle;

interlockable elements on the needle base and plunger for connecting the needle base to the plunger when the plunger tip is moved in the distal direction past a predetermined position, whereby, the needle base and plunger may be connected with each other, and the needle assembly can be drawn into the interior of the barrel by movement of the plunger in the proximal direction;

a projection on the plunger adjacent the plunger tip; and a resilient insert secured to the barrel adjacent the proximal end thereof, the plunger extending through the resilient insert and the resilient insert permitting movement of the plunger in the direction of elongation of the barrel, the resilient insert having a cam surface engageable by said projection on the plunger to expand the insert when the plunger is withdrawn past a predetermined position in the proximal direction and permit resilient contraction of the insert when the plunger moves farther in the proximal direction, the plunger and insert having latching surfaces which move past each other when the insert is expanded by the engagement of the cam surface by said projection, and which are engageable with each other when the insert is resiliently contracted after the plunger makes said movement farther in the proximal direction, to prevent distal movement of the plunger after the needle assembly is withdrawn into the interior of the barrel.

2. A safety syringe comprising:

a barrel elongated along an axis of elongation, said barrel having proximal and distal ends, a cylindrical interior wall, and openings at said proximal and distal ends;

a needle assembly comprising a hollow needle and a needle base, the needle base being removably held in the distal end opening of the barrel with the needle projecting therefrom externally of the barrel in the direction of elongation of the barrel;

a plunger extending through the proximal end opening of the barrel and having a resilient plunger tip sealingly engaged with the cylindrical interior wall of the barrel and slidable along said wall to draw fluid into the barrel through the needle and to expel fluid from the interior of the barrel through the needle;

interlockable elements on the needle base and plunger for connecting the needle base to the plunger when the plunger tip is moved in the distal direction past a predetermined position, whereby, the needle base and plunger may be connected with each other, and the needle assembly can be drawn into the interior of the barrel by movement of the plunger in the proximal direction; and interengageable surfaces in axially fixed relationship to said plunger and said barrel respectively, said interengageable surfaces comprising a proximally facing surface in a fixed position along the length of the barrel adjacent the proximal end of the barrel, and a distally facing surface in a fixed position along the length of the plunger adjacent the distal end of the plunger, said distally facing surface being movable in the proximal direction past said proximally facing surface as the plunger is moved in the proximal direction to draw the needle assembly into the interior of the barrel, but being engageable with said proximally facing surface to prevent distal movement of the plunger after the needle assembly is withdrawn into the interior of the barrel, said safety syringe including a resilient insert secured to the barrel adjacent the proximal end of the barrel, said insert including at least one radially movable part, in which said proximally facing surface is formed on said radially movable part, and including a cam arranged to press said radially movable part outward to allow said distally facing surface to move proximally past said proximally facing surface as the plunger is moved in the proximal direction to draw the needle assembly into the interior of the barrel.

* * * * *

UNITED STATES PATENT AND TRADEMARK OFFICE
CERTIFICATE OF CORRECTION

PATENT NO. : 6,821,266 B2
DATED : November 23, 2004
INVENTOR(S) : Abrar Solatch It is certified that error appears in the above-identified patent and that said Letters Patent is hereby corrected as shown below:

Title page,
Item [75], Inventors, delete "William R. Knepshield, Kennedyville, MD (US);".

Signed and Sealed this

Sixth Day of September, 2005

JON W. DUDAS
*Director of the United States Patent and Trademark Office*